(12) United States Patent
Xiao et al.

(10) Patent No.: US 7,101,367 B2
(45) Date of Patent: Sep. 5, 2006

(54) DEPLOYABLE CRYOSURGICAL CATHETER

(75) Inventors: Jia Hua Xiao, Bridgewater, NJ (US); Simon Cohn, North Arlington, NJ (US)

(73) Assignee: Ethicon, Inc., Somerville, NJ (US)

( * ) Notice: Subject to any disclaimer, the term of this patent is extended or adjusted under 35 U.S.C. 154(b) by 335 days.

(21) Appl. No.: 10/262,513

(22) Filed: Sep. 30, 2002

(65) Prior Publication Data

US 2004/0064134 A1 Apr. 1, 2004

(51) Int. Cl.
*A61B 18/18* (2006.01)

(52) U.S. Cl. .......................... 606/21; 606/23
(58) Field of Classification Search .............. 606/20–26
See application file for complete search history.

(56) References Cited

U.S. PATENT DOCUMENTS

| | | | |
|---|---|---|---|
| 5,449,380 A | * | 9/1995 | Chin ........................... 607/105 |
| 5,575,788 A | | 11/1996 | Baker et al. |
| 5,702,438 A | * | 12/1997 | Avitall ........................ 607/122 |
| 5,769,880 A | | 6/1998 | Truckai et al. |
| 5,916,213 A | | 6/1999 | Haissaguerre et al. |
| 6,068,629 A | | 5/2000 | Haissaguerre et al. |
| 6,161,047 A | | 12/2000 | King et al. |
| 6,197,022 B1 | | 3/2001 | Baker |
| 6,270,495 B1 | | 8/2001 | Palermo |
| 6,306,129 B1 | | 10/2001 | Little et al. |
| 6,475,212 B1 | * | 11/2002 | Dobak et al. ................. 606/23 |
| 6,547,784 B1 | * | 4/2003 | Thompson et al. ........... 606/21 |
| 6,620,161 B1 | | 9/2003 | Schulze et al. |
| 2003/0212389 A1 | * | 11/2003 | Durgin et al. ................ 606/21 |

OTHER PUBLICATIONS

Mosby–Year Book, Inc., M. Baggish, et al., "A Computer–Controlled, Continuously Circulating, Hot Irrigating System for Endometrial Ablation", Am. J. Obstet. Gynecol., vol. 173, No. 6, pp. 1842–1848 (Dec. 1995).

Pending U.S. patent application Ser. No. 10/278,466 entitled "RF Device for Treating the Uterus", filed Oct. 23, 2002, Inventors: Jia Hung Xiao, Thomas Ryan, Roddi Simpson and Alexander Sinton.

Pending U.S. patent application Ser. No. 10/186,259 entitled "RF Device for Treating the Uterus", filed Jun. 28, 2002, Inventors: Jia Hung Xiao, Thomas P. Ryan and Alexander J. Sinton.

Taylor & Francis Ltd., M.V. Prior, et al., "Treatment of Menorrhagia by Radiofrequency Heating", Int. J. Hyperthermia, vol. 7, No. 2, pp. 213–220 (1991).

The C.V. Mosby Co., W. Droegemueller, et al., "Cryocoagulation of the Endometrium at the Uterine Cornua", Am. J. Obstet. and Gynecol., vol. 131, No. 1, pp. 1–9 (May 1978).

American College of Obstetricians and Gynecologists, A. The Singer, et al., "Preliminary Clinical Experience with a Thermal Balloon Endometrial Ablation Method to Treat Menorrhagia", Obstet. Gynecol., vol.83, No. 5, Part 1, pp. 732–734, (May 1994).

* cited by examiner

*Primary Examiner*—Michael Peffley

(57) ABSTRACT

An expandable apparatus for use with a surgical probe having a temperature-controlled portion includes at least one thermally-conductive elongated extension member and means for thermally connecting and attaching the extension member to the surgical probe. The expandable apparatus further includes means for attaching and moving the extension member between a closed configuration in which the extension member is substantially parallel to the surgical probe and an open configuration in which the extension member extends radially outward from the surgical probe. A method of using the expandable apparatus to ablate tissue that line a body cavity is also disclosed.

15 Claims, 8 Drawing Sheets

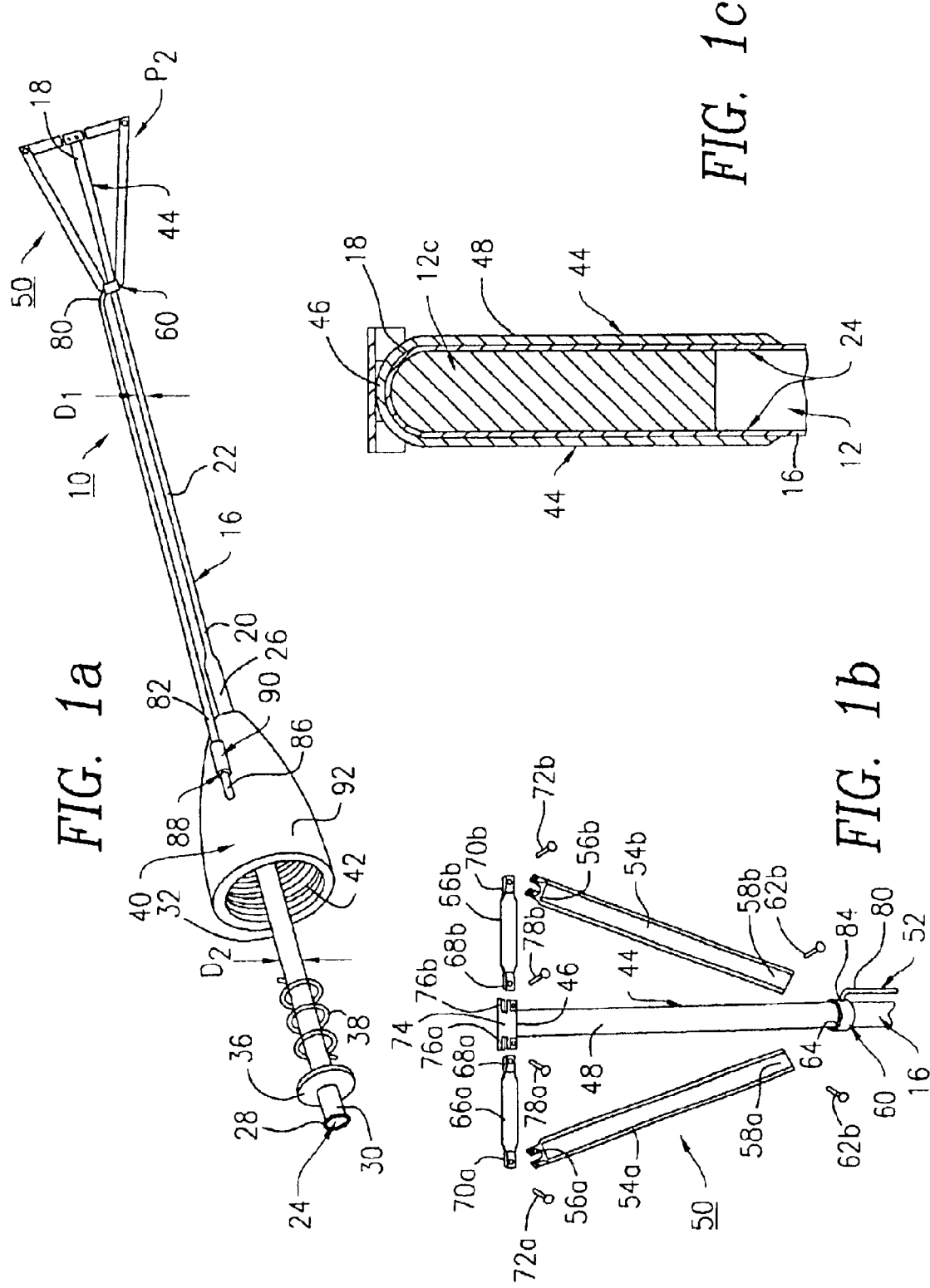

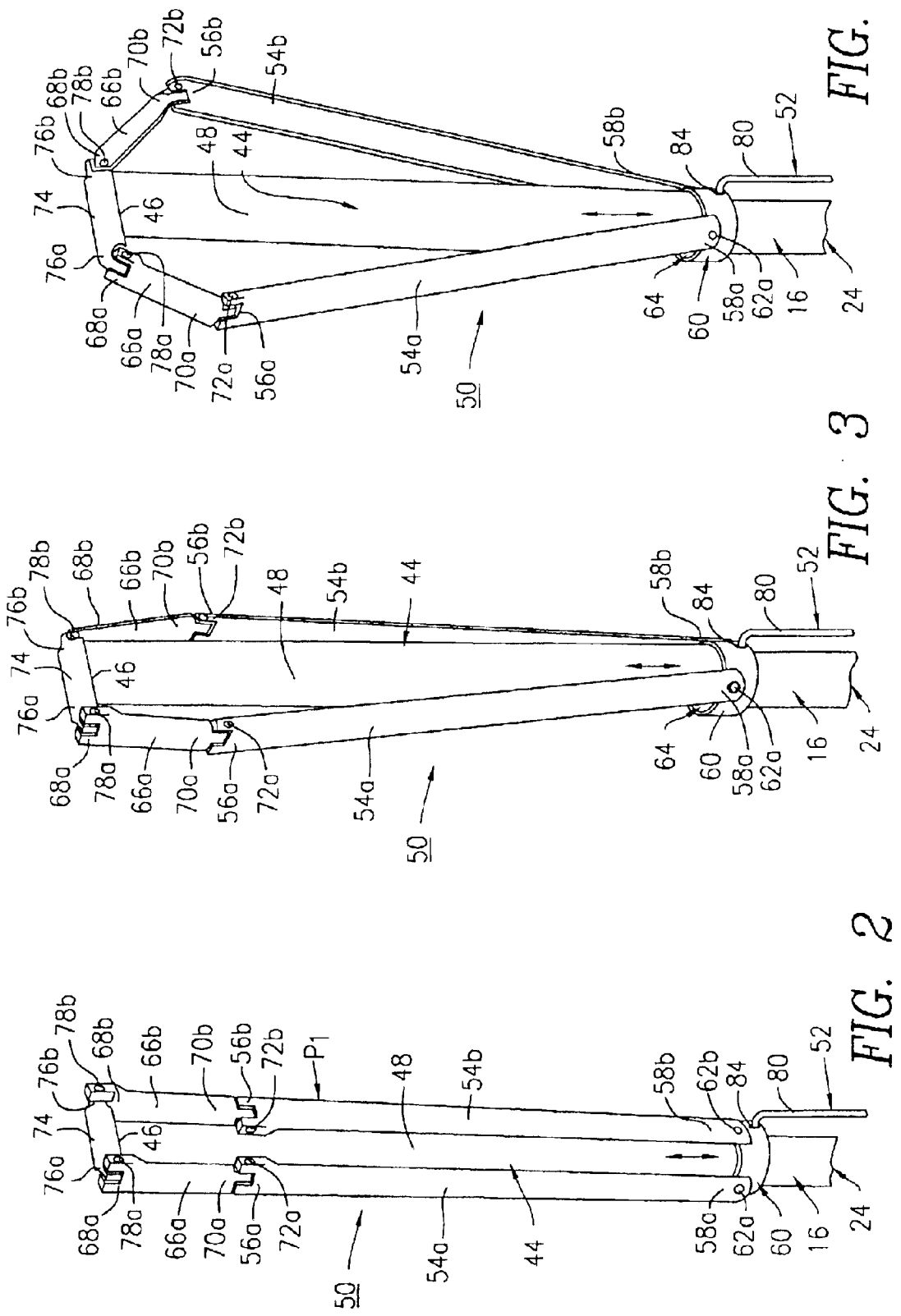

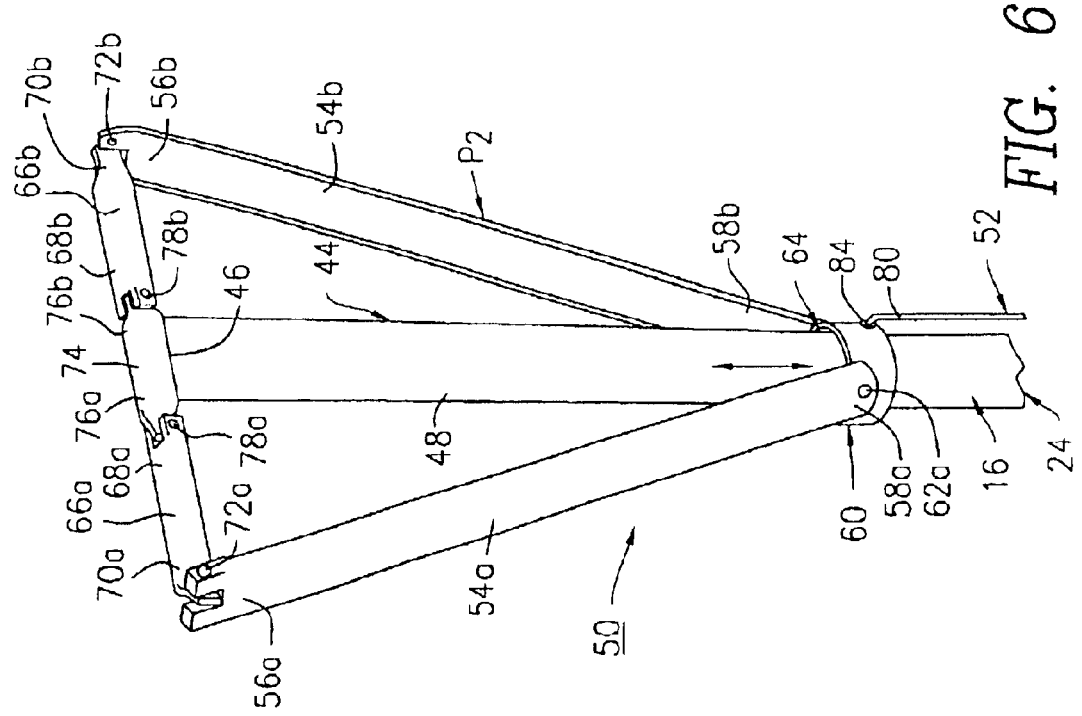
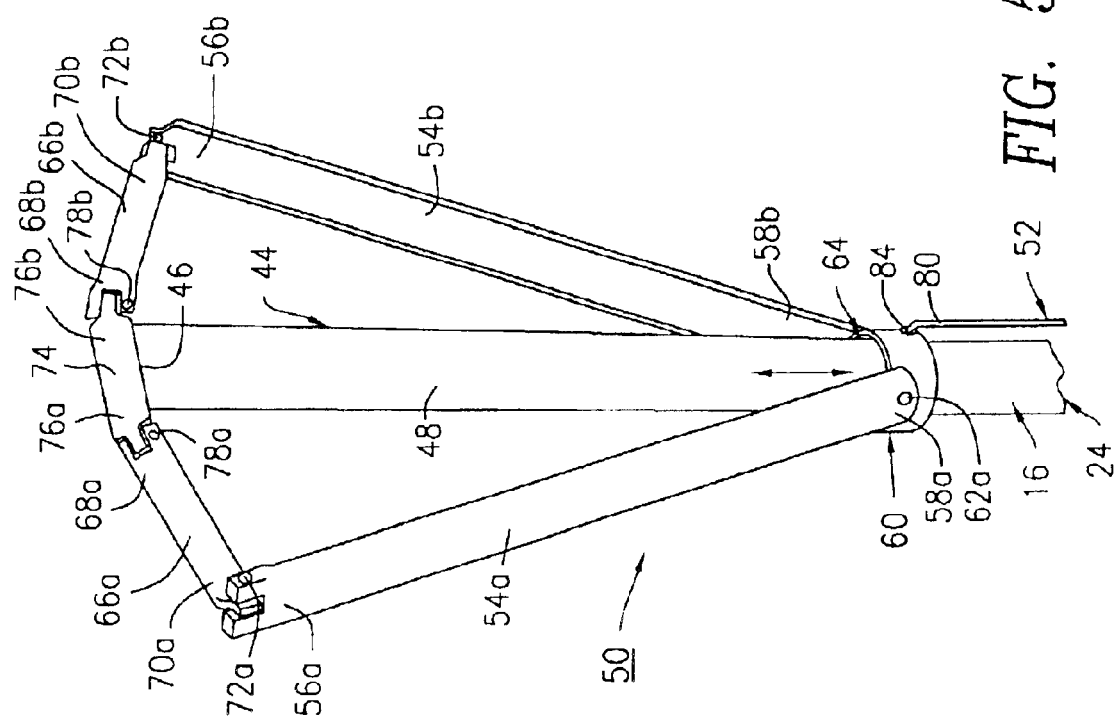

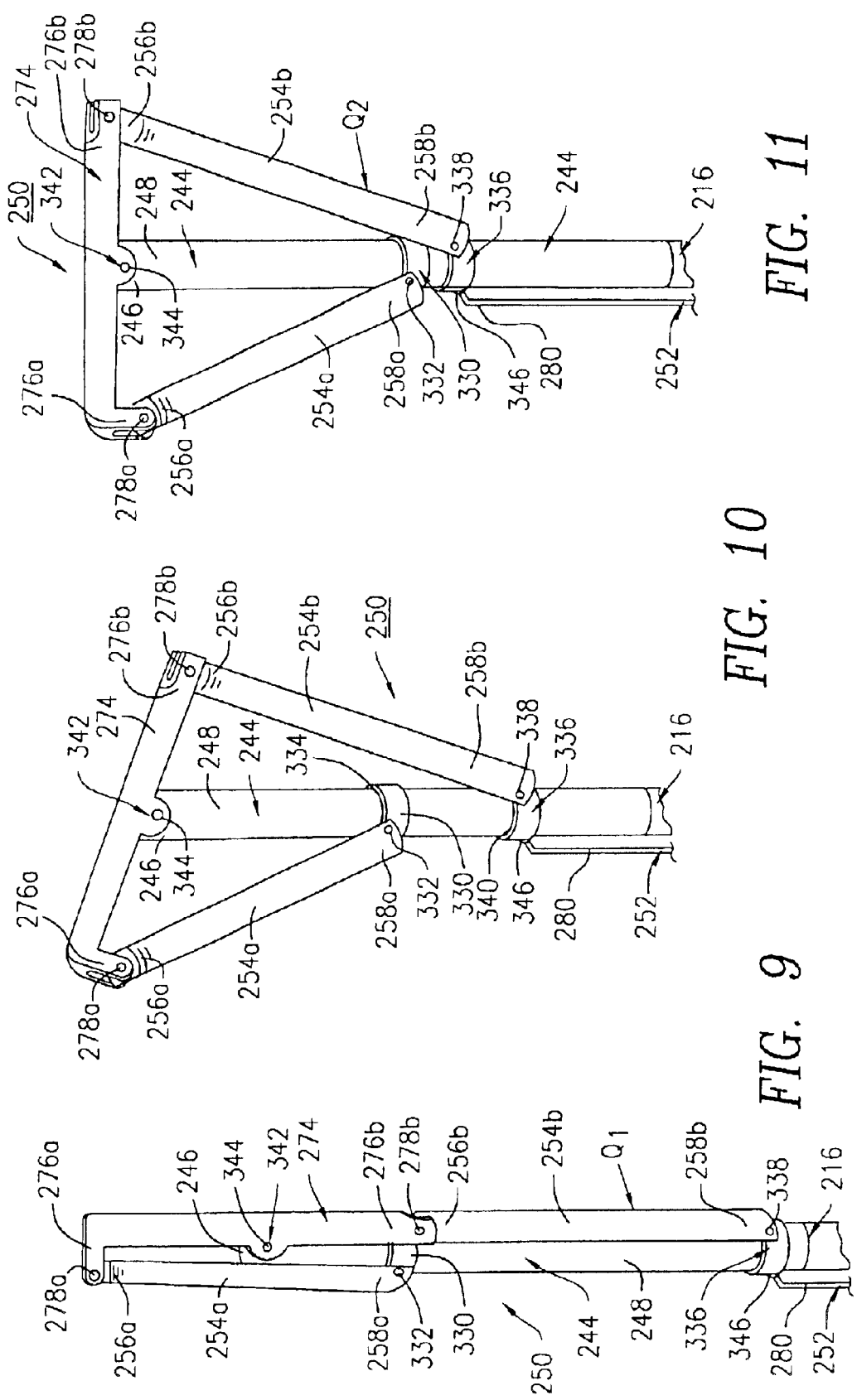

DEPLOYABLE CRYOSURGICAL CATHETER

FIELD OF THE INVENTION

The present invention relates to a deployable cryosurgical catheter suitable for performing intrauterine endometrial ablation. More particularly, the catheter has a deployable head having a source of cryogenic energy connected thereto.

BACKGROUND OF THE INVENTION

Endometrial ablation (i.e., the removal or destruction of the endometrial lining of the uterus) is used as an alternative to hysterectomy for treating abnormal uterine bleeding due to benign disease. The standard techniques for performing endometrial ablation employ a resectoscope (i.e., a hysteroscope with a built-in wire loop or other shaped device) that is inserted transcervically into the uterus, and uses radiofrequency electrical current (RF current) to remove or coagulate the endometrial tissue. These standard techniques typically are performed in a hospital setting.

During recent years, the medical industry has been developing simpler procedures, some of which are targeted for use in performing endometrial ablation in an office setting. Cryogenic ablation, or "cryoablation", is one such procedure. Cryoablation typically is performed using a straight, small-diameter probe, about 5 to 10 mm in diameter, that is inserted transcervically into the uterus. One such probe is described in U.S. Pat. No. 6,306,129. The probe is cooled to cryogenic temperatures, e.g., by circulation of a cryogenic fluid inside the probe. At a temperature of −90° C. or below, ice forms around the probe, freezing tissue in the endometrium (i.e., the lining) and myometrium (i.e., the muscle layer below the lining) of the uterus. The edge of the ice formation has a temperature of about 2° C., which is non-destructive of tissue. At a distance of about 4 mm within the ice ball, the temperature is about −20° C., which is sufficiently cold to destroy the endometrial tissue. A number of placements of the probe may be needed to destroy the lining of the entire cavity, but, typically, 2 to 3 ice balls are sufficient. Placement of the probe and formation of the ice ball can be visualized by abdominal ultrasound or other non-invasive imaging techniques. Such visualization facilitates complete ablation of the entire cavity and allows the doctor to control the formation of the ice ball to prevent unwanted tissue damage, e.g., freezing of the uterine serosa or other tissues surrounding the uterus.

A disadvantage of the cryoablation techniques known to the art arises from the need to create multiple ice formations to ablate the entire lining of the uterus. This need arises primarily because of the approximately triangular shape of the uterus and the volume of the uterus, which is too large to treat with a single ice ball. While it is usually practical to withdraw the probe from the surrounding ice ball, the presence of the ice formation within the uterus can make it difficult, if not impossible, to correctly position the probe for formation of the second or third ice formation. The withdrawal and repositioning of the probe also requires a significant amount of time.

There remains a need for a cryoablation tool that can be used to treat the entire intrauterine surface in a single freezing step. Moreover, the tool, as well as the procedures in which it is employed, should be suitable for use in a doctor's office.

SUMMARY OF THE INVENTION

The present invention overcomes the disadvantages and shortcomings of the prior art discussed above by providing a new and improved expandable apparatus for use with a surgical probe having a temperature-controlled portion and a method of using such apparatus to ablate tissue that line a body cavity. More particularly, the expandable apparatus includes at least one thermally-conductive elongated extension member and means for thermally connecting and attaching the extension member to the surgical probe. The expandable apparatus also includes means for attaching and moving the extension member between a closed configuration in which the extension member is substantially parallel to the surgical probe and an open configuration in which the extension member extends radially outward from the surgical probe.

BRIEF DESCRIPTION OF THE DRAWINGS

Further objects, features and advantages of the present invention will become apparent upon consideration of the following detailed description of the exemplary embodiments considered in connection with the accompanying drawings, in which:

FIG. 1a is a perspective view of the cryosurgical catheter of FIG. 1 with the proximal end of the catheter exposed;

FIG. 1b is an exploded view of the head of the cryosurgical catheter of FIG. 1 in an opened configuration;

FIG. 1c is a partial cross-sectional view of the catheter head of FIG. 1b showing a cold finger section of a cryogenic probe within the catheter head;

FIG. 2 is a perspective view of the head of the cryosurgical catheter of FIG. 1 in a closed, undeployed configuration;

FIG. 3 is a perspective view of the catheter head of FIG. 2 in a one-quarter-opened configuration;

FIG. 4 is a perspective view of the catheter head of FIG. 2 in a half-opened configuration;

FIG. 5 is a perspective view of the catheter head of FIG. 2 in a three-quarters-opened configuration;

FIG. 6 is a perspective view of the catheter head of FIG. 2 in a fully-opened configuration;

FIG. 9 is a perspective view of the head of the cryosurgical catheter of FIG. 8 in a closed, undeployed configuration;

FIG. 10 is a perspective view of the catheter head of FIG. 9 in a partially-opened configuration;

FIG. 11 is a perspective view of the catheter head of FIG. 9 in a fully-opened configuration.

DETAILED DESCRIPTION OF THE EXEMPLARY EMBODIMENTS

Figure 1:
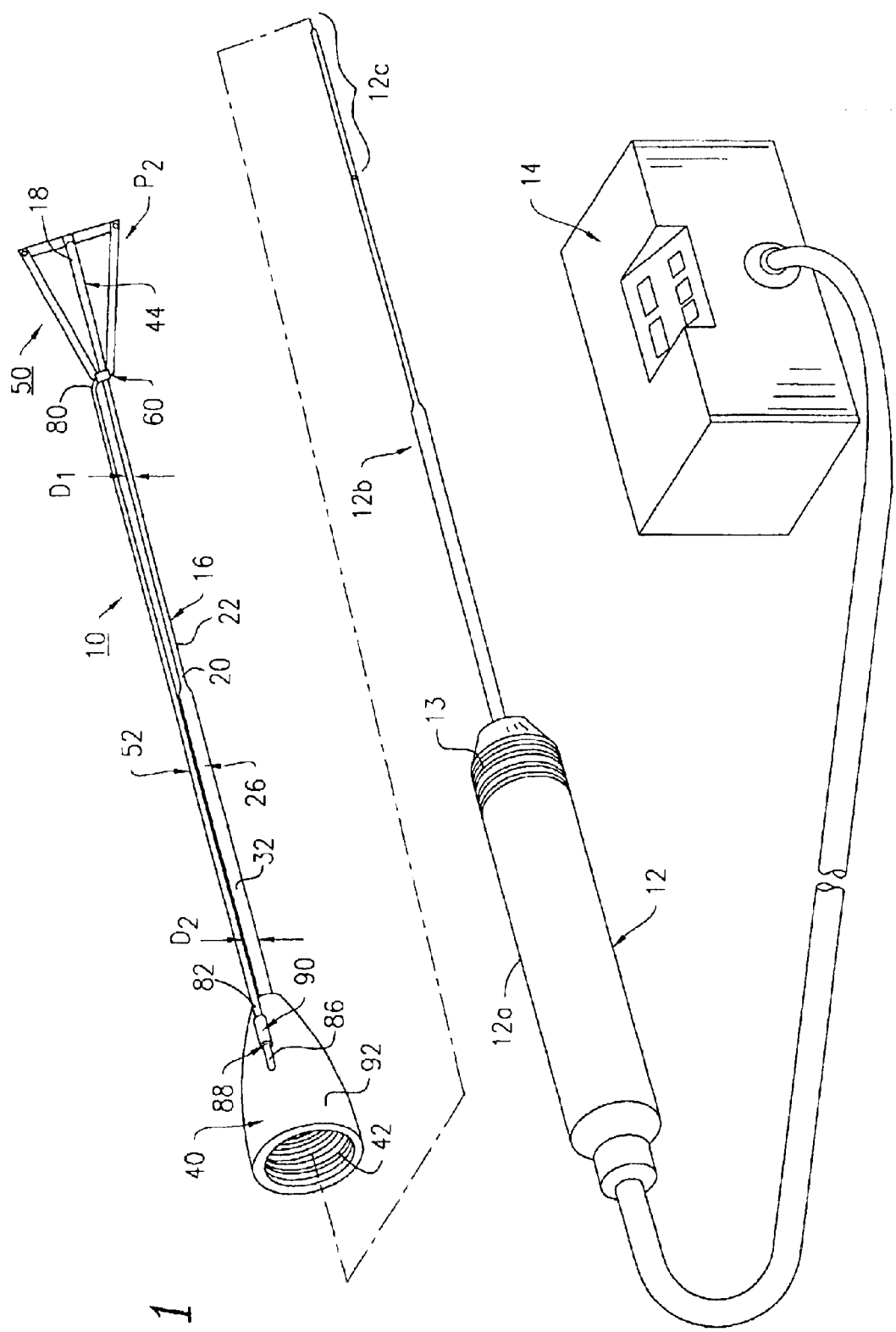
FIG. 1 is a perspective view of a cryosurgical catheter constructed in accordance with a first exemplary embodiment of the present invention and a cryogenic probe of a type known in the art.

Referring to FIG. 1, there is shown a deployable cryosurgical catheter device 10 and a cryogenic probe 12 connected to a cryogenerator 14. The cryogenic probe 12 has a handle portion 12a having a threaded fitting 13 thereon, and an elongated member 12b which has a region of high thermal conductivity, or "cold finger" section 12c, preferably at the distal end of the probe 12. The cryosurgical device 10 includes a catheter 16, which, preferably, has an outer diameter $D_1$ of less than 5 mm and, preferably, is made from a material having a high thermal conductivity. The catheter 16 has a distal end 18, a proximal end 20, an outer wall surface 22 and an interior channel opening 24 (see FIG. 1c) that is adapted to receive the elongated member 12b of probe 12. The distal end 18 is preferably made of a material having a high thermal conductivity, e.g., a thin-wall stainless steel tube made of some other metal. The proximal end 20 of catheter 16 includes an integrally-formed wide catheter portion 26 having a proximal end 30 with a beveled/chamfered rim 28 and an outer wall surface 32 (see FIG. 1a). The wide catheter portion 26 has an outer diameter $D_2$ which is larger than the outer diameter $D_1$ of catheter 16. As seen in FIG. 1a, the proximal end 30 of wide catheter portion 26 includes a washer 36 that receives the wide portion 26 of catheter 16 and is affixed thereto, a connector sleeve 40 having interior spiral threads 42 and receiving the wide portion 26 of catheter 16, and a compression spring 38 that surrounds the wide portion 26 of catheter 16 and is positioned between the washer 36 and the connector sleeve 40. The threads 42 are adapted for connection to the threaded fitting 13 of the cryogenic probe 12. The distal end 18 of catheter 16 includes an end section 44, that is adapted to encompass the cold finger section 12c of cryogenic probe 12 (see FIG. 1c). The end section 44 includes a tip 46 and an outer wall surface 48. The tip 46 is attached, in a manner described more fully hereinafter, to a catheter head 50 that has a closed configuration $P_1$ (see FIG. 2) and a fully-opened configuration $P_2$ (see FIG. 6). In the illustrated, preferred embodiment, the fully-opened configuration $P_2$ of catheter head 50 has a substantially triangular shape that approximates the interior dimensions of a uterine cavity. The deployable cryosurgical catheter 10 includes an actuator rod 52, which may be used to move the catheter head 50 between the fully-closed configuration $P_1$ (see FIG. 2) and the fully-opened configuration $P_2$ (see FIG. 6) through a range of intermediate configurations (see FIGS. 3–5).

With reference to FIG. 1b, the catheter head 50 includes a pair of legs 54a, 54b. Leg 54a has a distal end 56a and a proximal end 58a, the proximal end 58a being attached to a collar 60 by a pivot pin 62a. Leg 54b has a distal end 56b and a proximal end 58b, the proximal end 58b being attached to the collar 60 by a pivot pin 62b. The collar 60 includes an axial opening 64 which receives the end section 44 of catheter 16 such that collar 60 can slide freely along end section 44. The legs 54a, 54b are movable between a closed configuration (see FIG. 2), in which the legs 54a, 54b are adjacent to the end section 44, and an opened configuration (see FIG. 6), in which the distal ends 56a, 56b of legs 54a, 54b are spaced apart from each other in a V-shaped arrangement. Preferably, the legs 54a, 54b are made of a material having a high thermal conductivity, e.g., copper metal or other metals, which may be coated or plated with another biocompatible material and each leg 54a, 54b has a concave cross-sectional shape such that the legs 54a, 54b fit closely against the end section 44 when the legs 54a, 54b are in their closed configuration.

The catheter head 50 further includes a pair of arm segments 66a, 66b. Arm segment 66a has an inner end 68a and an outer end 70a that is hingedly attached to the distal end 56a of the leg 54a by a hinge pin 72a. Arm segment 66b has an inner end 68b and an outer end 70b that is hingedly attached to the distal end 56b of the leg 54b by a hinge pin 72b. Each of the arm segments 66a, 66b is movable between a closed configuration (see FIG. 2) in which the arm segments 66a, 66b are adjacent to the end section 44, and an opened configuration (see FIG. 6), in which the outer ends 70a, 70b of arm segments 66a, 66b pivot about the distal ends 56a, 56b of legs 54a, 54b, respectively, such that the outer ends 70a, 70b and the inner ends 68a, 68b all are arranged in a substantially straight line. Preferably, the arm segments 66a, 66b are made of a material having a high thermal conductivity, e.g., copper metal or other metals, which may be coated or plated with another biocompatible material, and each arm 66a, 66b has a concave cross-sectional shape such that the arms 66a, 66b fit closely against the end section 44 when the arms 66a, 66b are in their closed configuration. The outer diameter of the fully-closed catheter head 50, preferably, is less than 10 mm. The maximum width of the fully-opened catheter head 50 should be between about 20 mm and 34 mm.

The catheter head 50 also includes a distal connecting member 74 that is affixed to the tip 46 of the end section 44 of catheter 16 (see FIGS. 1b and 1c). The connecting member 74 has opposing outer ends 76a, 76b. The outer end 76a of connecting member 74 is hingedly attached to the inner end 68a of arm segment 66a by a hinge pin 78a. The outer end 76b of connecting member 74 is hingedly attached to the inner end 68b of arm segment 66b by a hinge pin 78b. Preferably, the connecting member 74 is made of a material having a high thermal conductivity, e.g., copper metal or other metals, which may be coated or plated with another biocompatible material, The actuator rod 52 is configured to slide the collar 60 axially along the length of the outer wall surface 48 of the end section 44. Referring again to FIG. 1, the actuator rod 52 has a distal end 80 and a proximal end 82. The distal end 80 of actuator rod 52 is attached to the sliding collar 60 by a connector pin 84 (see FIG. 2). The proximal end 82 of actuator rod 52 includes a finger grip member 86 adapted to be grasped between the fingers of an operator, such as a medical practitioner. A connector ring 90 having an opening 88 is attached to an outer wall surface 92 of the connector sleeve 40. The proximal end 82 of the actuator rod 52 is received within the opening 88 so that the actuator rod 52 may slide through the opening 88. Preferably, the actuator rod 52 is made of a material having a very low thermal conductivity.

Referring to FIGS. 1 and 1a, the cryogenic probe 12 is received within the channel opening 24 of the catheter 16 through the wide catheter portion 26, so that the cold finger section 12c of the cryogenic probe 12 is in sufficiently close contact with end section 44 and the tip 46 of the catheter 16 (see FIG. 1c) to enable rapid temperature equalization between the cold finger section 12c of the cryogenic probe 12 and the outer wall surface 48 of the end section 44. A thermally conductive grease may be used to fill any gap between the surfaces of the cold finger section 12c and the end section 44 of the catheter 16 to increase the rate of temperature equalization. The connector sleeve 40 is tightened onto the threaded fitting 13 of the cryogenic probe 12, so that the washer 36 and compression spring 38 maintain secure contact between the cryogenic probe 12 and the wide portion 26 of the catheter 16.

A second exemplary embodiment of the present invention is illustrated in FIGS. 8 to 12. Elements illustrated in FIGS. 8 to 12 that correspond to the elements described above with reference to FIGS. 1 to 7 have been designated by corresponding reference numbers increased by two hundred. The second embodiment is constructed and operates in the same manner as the first embodiment, unless otherwise stated herein.

Figure 8:
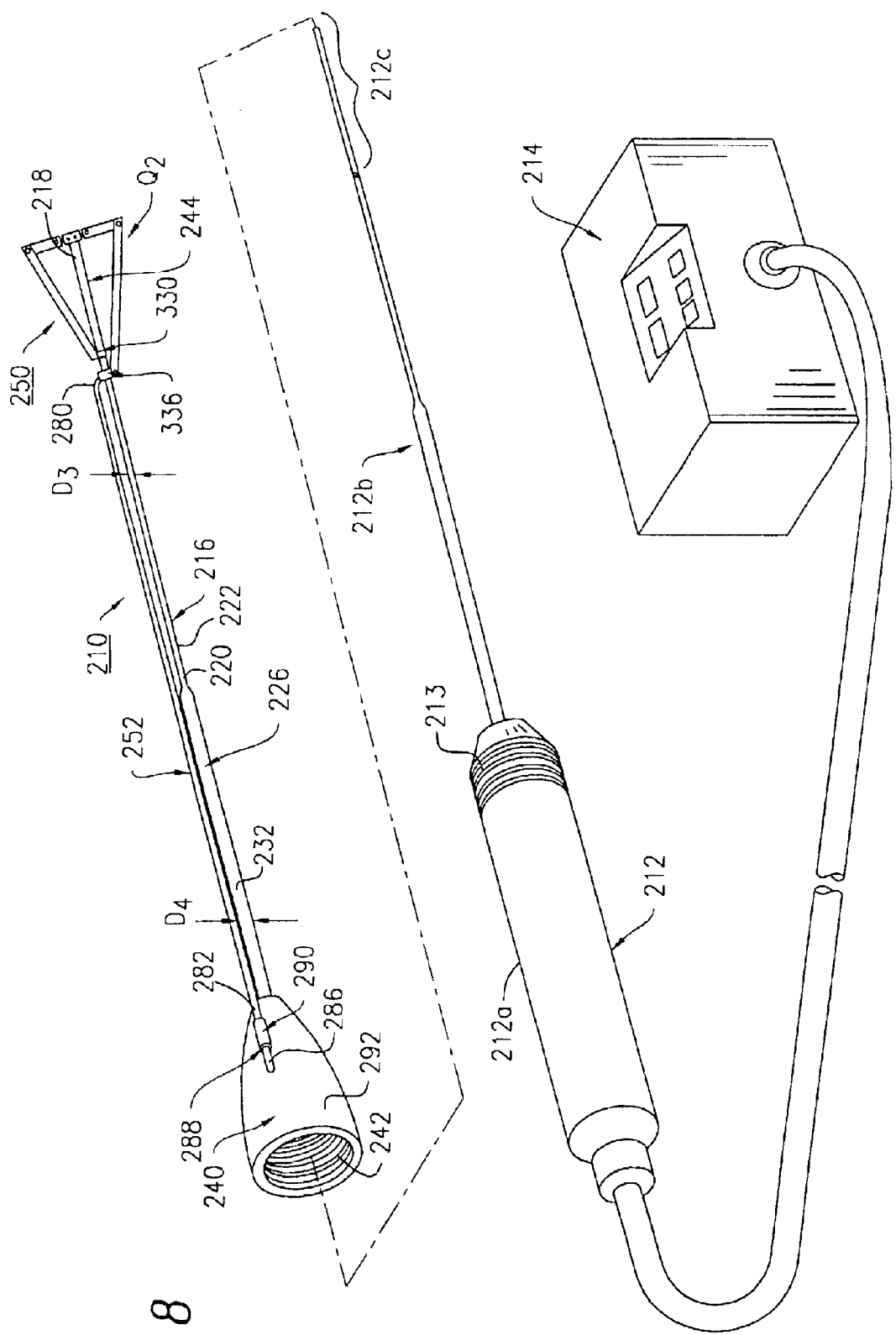
FIG. 8 is a perspective view of a cryosurgical catheter constructed in accordance with a second exemplary embodiment of the present invention and a cryogenic probe of a type known in the art.

Referring to FIG. 8, there is shown a deployable cryosurgical catheter device 210 and a cryogenic probe 212 connected to a cryogenerator 214. The cryogenic probe 212 has a handle portion 212a having a threaded portion 213 thereon, and an elongated member 212b which has a region of high thermal conductivity, or "cold finger" section 212c, preferably at the distal end of the probe 212. The cryosurgical device 210 includes a sheath or catheter 216, which, preferably, has an outer diameter $D_3$ of less than 5 mm, and, preferably, is made from a material having a high thermal conductivity, e.g., thin wall tube made of stainless steel or another metal. The catheter 216 has a distal end 218, a proximal end 220, an outer wall surface 222 and an interior channel opening (not shown) that is adapted to receive the elongated member 212b of probe 212. The proximal end 220 of catheter 216 includes an integrally-formed wide catheter portion 226 having similar elements to the wide catheter portion 26 illustrated in FIG. 1a. The wide catheter portion 226 has an outer diameter $D_4$ which is larger than the outer diameter $D_3$ of catheter 216. A connector sleeve 240 having interior spiral threads 242 receives the wide portion 226 of catheter 216. The threads 242 are adapted for connection to the threaded portion 213 of the cryogenic probe 12. The distal end 218 of catheter 216 includes an end section 244, preferably copper-clad, which is adapted to encompass the cold finger section 212c of cryogenic probe 212. The end section 244 includes a tip 246 and an outer wall surface 248 (see FIG. 11). The tip 246 is attached, in a manner described more fully hereinafter, to a catheter head 250 that has a fully-closed configuration $Q_1$ (see FIG. 9) and a fully-opened configuration $Q_2$ (see FIG. 11). In the illustrated, preferred embodiment, the fully-opened configuration $Q_2$ of catheter head 250 has a substantially triangular shape that approximates the interior dimensions of a uterine cavity. The deployable cryosurgical catheter 210 includes an actuator rod 252, which may be used to move the catheter head 250 between the fully-closed configuration $Q_1$ and the fully-opened configuration $Q_2$ through an intermediate configuration (see FIG. 10).

With reference to FIGS. 9–11, the catheter head 250 includes a pair of legs 254a, 254b. Leg 254a has a distal end 256a and a proximal end 258a that is attached to a first collar 330 by a pivot pin 332. Leg 254b has a distal end 256b and a proximal end 258b that is attached to a second collar 336 by a pivot pin 338. The first collar 330 includes a first axial opening 334 that receives the end section 244 of catheter 216 such that the first collar 330 can slide freely along the end section 244. The second collar 336 includes a second axial opening 340 that receives the end section 244 of catheter 216 such that the second collar 336 can slide freely along the end section 244. The second collar 336 is located proximally in relation to the first collar 330. The legs 254a, 254b are movable between a closed configuration (see FIG. 9), in which the legs 254a, 254b are adjacent to the end section 244 and the first collar 330 and the second collar 336 are at their greatest distance from each other, and an opened configuration (see FIG. 11), in which the distal ends 256a, 256b of legs 254a, 254b, respectively, are spaced apart from each other in a V-shaped arrangement and the first collar 330 and second collar 336 are in their closest proximity to each other. Preferably, the legs 254a, 254b are made of a material having a high thermal conductivity, e.g., copper metal or other metals, and each leg 254a, 254b has a concave cross-sectional shape such that the legs 254a, 254b fit closely against the end section 244 when the legs 254a, 254b are in their closed configuration.

Referring to FIG. 11, the catheter head 250 further includes a distal connecting member 274 having opposing outer ends 276a, 276b. The connecting member 274 includes a central pivot opening 342 and is attached to the tip 246 of the end section 244 of catheter 216 by a pivot pin 344 at the central pivot opening 342. The outer end 276a of the connecting member 274 is hingedly attached to the distal end 256a of leg 254a by a hinge pin 278a. The outer end 276b of the connecting member 274 is hingedly attached to the distal end 256b of leg 254b by a hinge pin 278b. The connecting member 274 is moveable between the fully-closed configuration $Q_1$ (see FIG. 9) in which the connecting member 274 and the legs 254a, 254b are adjacent to the end section 244, and the fully-opened configuration $Q_2$ (see FIG. 11) in which the distal ends 256a, 256b of the legs 254a, 254b are spaced away from the end section 244. During such movement, the connecting member 274 pivots about the tip 246 of the catheter 216 and its outer ends 276a, 276b pivot about the distal ends 256a, 256b of legs 254a, 254b, respectively, such that the distal end 276a moves relative to the distal end 276b and the first collar 330 slides along the length of the end section 244 of catheter 216. In the fully-opened configuration $Q_2$, catheter head 250 has a substantially triangular shape with legs 254a, 254b and the connecting member 274 forming the sides of the triangle. As can be seen in FIGS. 9–11, the leg 254a is somewhat shorter than the leg 254b to compensate for the spacing between the first collar 330 and the second collar 336 in the fully-opened configuration $Q_2$.

The actuator rod 252 is configured to slide the second collar 336 axially along the length of the outer wall surface 248 of the end section 244. Referring again to FIG. 8, the actuator rod 252 has a distal end 280 and a proximal end 282. The distal end 280 of actuator rod 252 is attached to the second sliding collar 336 by a connector pin 346 (see FIGS. 9–11). The proximal end 282 of the actuator rod 252 includes a finger grip member 286 adapted to be grasped between the fingers of an operator, such as a medical practitioner. A connector ring 290 having an opening 288 is attached to an outer wall surface 292 of the connector sleeve 240. The proximal end 282 of the actuator rod 252 is received within the opening 288 so that the actuator rod 252 may slide through the opening 288.

The insertion of the elongated member 212b of the cryogenic probe 212 and the connection of the connecting sleeve 240 to the probe handle 212a is performed in the manner described for the first embodiment of FIG. 1.

Figure 7:
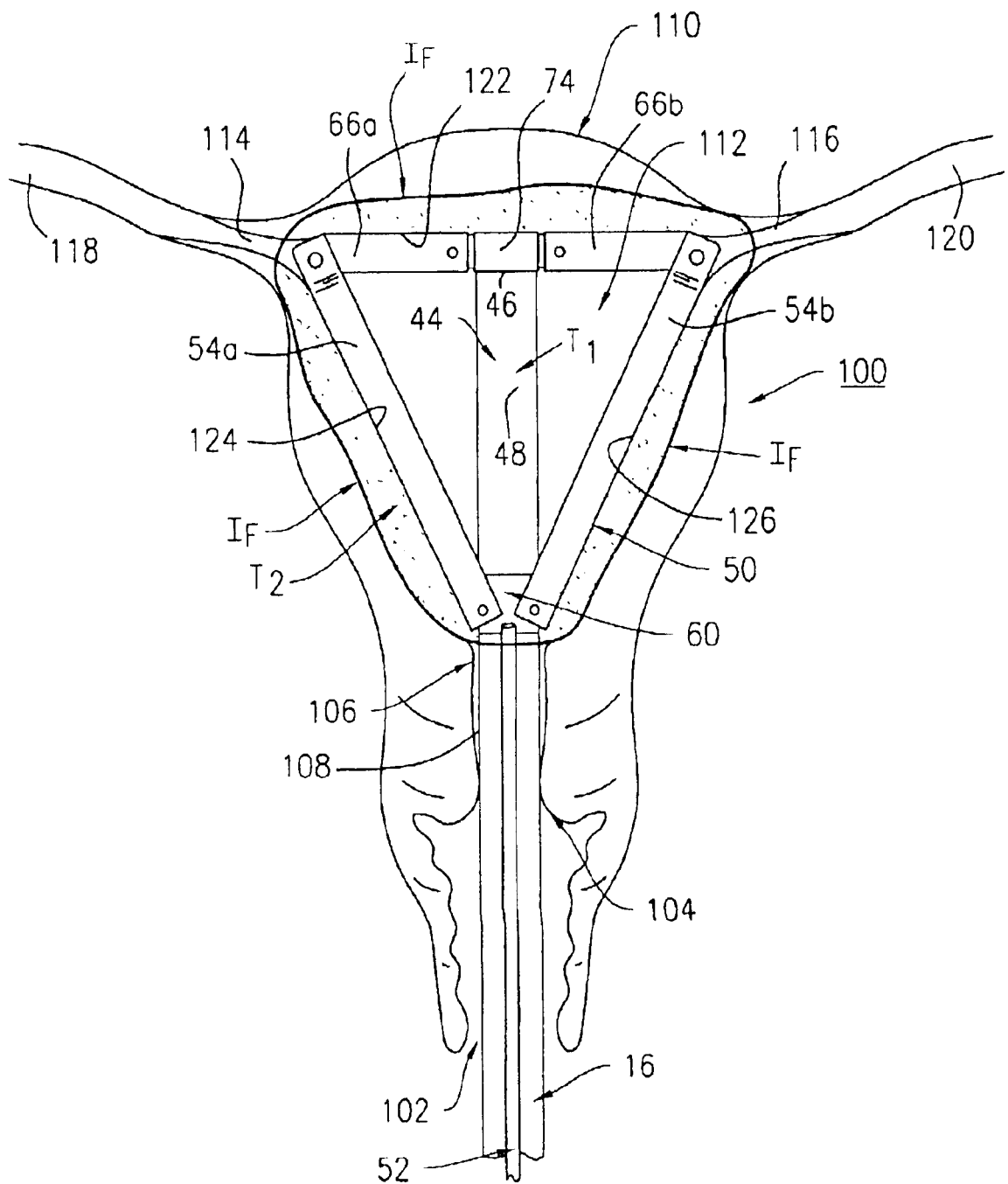
FIG. 7 is a cross-sectional view of the cryosurgical catheter of FIG. 1 showing the deployment of the catheter head in a fully-opened configuration within a uterine cavity.

A brief overview of the female reproductive system, with reference to FIG. 7, is presented herein to aid in describing the use of the cryosurgical catheter device 10 in performing an intrauterine endometrial ablation. The female reproductive system 100 includes a vaginal canal 102, an external cervical opening 104, a cervix 106 having a cervical canal 108; a uterus 110 having a uterine cavity 112; tubal ostia 114, 116; and Fallopian tubes 118, 120. The Fallopian tubes 118, 120 are connected to the uterine cavity 112 via the tubal ostia 114, 116. As illustrated in FIG. 7, the uterine cavity 112 in cross-section has a substantially triangular shape and includes a top wall (hereinafter referred to as a fundus 122) and side walls 124, 126.

The deployable cryosurgical catheter device 10 may be operated to perform an intrauterine endometrial ablation with a single insertion and freezing cycle. Before inserting the cryoprobe, a certain amount (a few cubic centimeters) of biocompatible fluid, such as a saline solution, or a gel may be injected into the uterine cavity to facilitate the freeze process inside the cavity. With reference to FIG. 1, a cryogenic probe 12 is interfitted with a sterilized deployable cryosurgical catheter 10. The catheter head 50, in its fully-closed configuration $P_1$ (see FIG. 2), is inserted transcervically through the cervical canal 108 and into the uterine cavity 112 of the uterus 110. The catheter 10 is advanced to place the distal connecting member 74 adjacent to and, preferably, in physical contact with the fundus 122 of the uterine cavity 112.

The operator then deploys the catheter head 50 within the uterine cavity 112 by pushing the finger grip member 86 of the actuator rod 52 axially toward the catheter head 50. The actuator rod 52 pushes the collar 60 in a distal direction along the length of the end section 44 of the catheter 16. Referring to FIGS. 2–6, as the collar 60 moves distally, the proximal ends 58a, 58b of the legs 54a, 54b, respectively, are also moved distally, causing the proximal ends 58a, 58b to pivot about the pins 62a, 62b and the distal ends 56a, 56b of the legs 54a, 54b, respectively, to pivot about the pins 72a, 72b. At the same time, the proximal ends 70a, 70b of the arms 66a, 66b, respectively, are pushed distally by the legs 54a, 54b, causing the proximal ends 70a, 70b to also pivot about the pins 72a, 72b, respectively. The distal ends 68a, 68b of the arms 66a, 66b, respectively, pivot about the distal connecting member 74 which is rigidly affixed to the tip 46 of the catheter 16. The result of the aforementioned movements is that, as the collar 60 is moved along the length of the end section 44, the legs 54a, 54b and the arms 66a, 66b swing outwardly from the end section 44, thereby deploying the catheter head 50 from its fully-closed configuration $P_1$ to its fully-opened configuration $P_2$ through a range of intermediate configurations, as depicted in FIGS. 2–6. Preferably, the legs 54a, 54b and the arms 66a, 66b are dimensioned so that they are near to, or, more preferably, in contact with, the fundus 122 and the side walls 124, 126 of the uterine cavity 112 when the catheter head 50 is in its fully-opened configuration $P_2$ (see FIG. 7).

After the catheter head 50 has been deployed to its fully-opened configuration $P_2$, the cold finger section 12c of the probe 12 is cooled to a cryogenic temperature $T_1$ of −90° C. or below, preferably, by supplying a cold fluid to the probe 12 from a cryogenerator 14. As described above, the cold finger 12c is in direct contact with the end section 44 of the catheter 16. The end section 44 is made of a material having a high thermal conductivity, as are the legs 54a, 54b, the arms 66a, 66b, and the connecting member 74 of the catheter head 50. Therefore, the temperatures of the end section 44 and the components of the catheter head 50 rapidly attain equilibrium with the temperature of the cold finger 12c, i.e., the end section 44 and catheter head 50 are rapidly cooled to a cryogenic temperature. An ice formation IF rapidly builds up around the catheter head 50. The ice also fills any gaps that may be present between the components of the catheter head 50, e.g., a gap between an arm and a leg where the two components are joined or the gap between a leg and the end section 44. The formation of the ice facilitates rapid freezing of the uterine tissue as the thermal conductivity of the ice is much higher than the thermal conductivity of the air or body fluid or water that would otherwise fill the gaps.

Heat is continually removed from the uterine cavity and the adjacent tissues, with the heat transfer being driven by the temperature gradients between the uterine tissues at temperature $T_2$ and the cryogenic temperature $T_1$ of the cold finger 12c. The ice front $I_F$ extends into the fundus 122 and side walls 124, 126 of the uterus 112 as the uterine tissues are cooled below their freezing temperature. At this point in the process, the ice front $I_F$ expands at a uniform rate outwardly from the catheter head 50. The rate at which the tissue freezes is controlled by the temperature gradient between $T_2$ and the temperature at the edge of the ice formation, and the rate at which heat is removed by the probe 12. The triangular shape of the fully-opened catheter head 50 approximates the shape of the uterine cavity 112, allowing the entire lining of the uterus 110 to be ablated in a single freezing step.

The expansion of the frozen zone can be visualized, as it occurs, by imaging techniques such as ultrasound imaging or magnetic resonance imaging (MRI). The same techniques can be used to observe the placement and deployment of the catheter head 50. It is particularly important to monitor the extent of the ice front $I_F$ to ensure that the endometrium is destroyed while the myometriumonly sustains only minimal damage with no damage to the serosa and any other surrounding tissues. Experience with conventional cryosurgical techniques has shown that the temperature at the edge of the ice formation typically is about 2° C., which is non-destructive of tissue. At a distance of about 4 mm within the ice front $I_F$, the temperature is about −20° C., which is sufficiently cold to destroy the endometrial tissue. Therefore, the cryogenic treatment should be stopped when the ice front $I_F$ has penetrated the myometrium to a depth of about 7 to 10 mm. Appropriate care should be taken to avoid freezing the serosa, or outermost layer, of the uterus 110 to avoid permanent, unwanted damage to the integrity of the uterus and the surrounding tissues.

After the desired degree of ablation has been achieved, delivery of the cold fluid is stopped and a warmer fluid is supplied to the cold finger 12c to thaw the ice front $I_F$ around the catheter head 50.

When the ice front $I_F$ has been sufficiently thawed, the catheter head 50 is collapsed to its fully-closed configuration $P_1$ by pulling the finger grip member 86 axially in a direction away from the catheter head 50. The collar 60 slides along the length of the end section 44 in a proximal direction, causing the legs 54a, 54b and the arms 66a, 66b to move in directions opposite to their directions of movement during the deployment of the catheter head 50. The fully-closed catheter head 50 is then removed from the uterine cavity 112 through the cervical canal 108 and detached from the probe 12. The cryosurgical catheter device 10 may then be destroyed or sterilized by conventional means for re-use.

Figure 12:
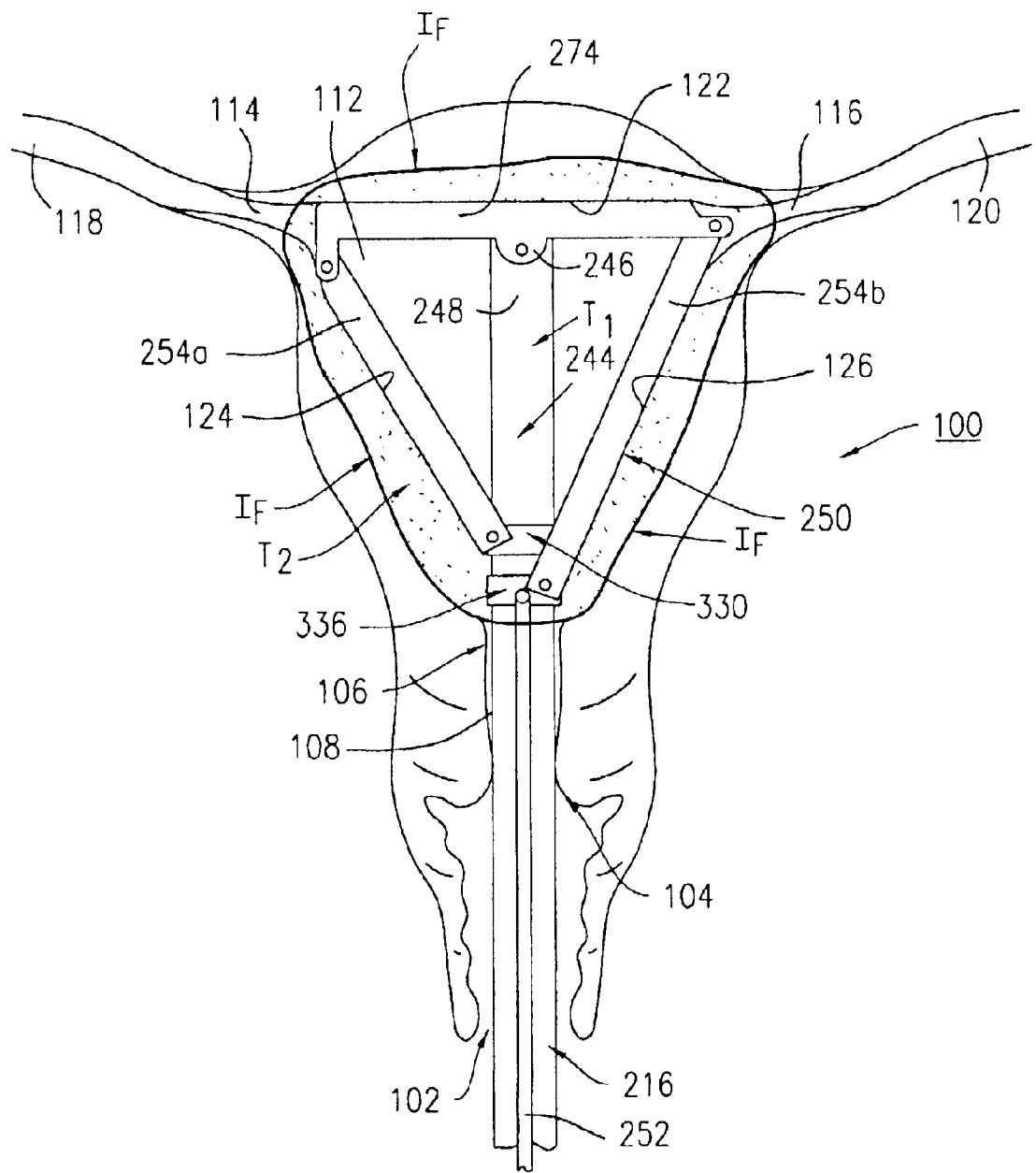
FIG. 12 is a perspective view of the cryosurgical catheter of FIG. 8 showing the deployment of the catheter head in a fully-opened configuration within a uterine cavity.

The deployable cryosurgical catheter device 210 illustrated in FIG. 12 may be operated in the same way as the cryosurgical catheter device 10, except for the manner in which the catheter head 250 is deployed to its fully-opened configuration $Q_2$. The catheter head 250 is initially in its fully-closed configuration $Q_1$ (see FIG. 9). The catheter head 250 is advanced toward the fundus 122 until the distal ends 256a, 256b of the legs 254a, 254b, respectively, and the connecting member 274 are set off from the fundus 122 by a small distance (approximately 10 mm). The offset should be sufficient to allow the outer ends 276a, 276b of the connecting member 274 to pivot about the distal ends 256a, 256b of the legs 254a, 254b, respectively, without contacting the fundus 122. The operator then deploys the catheter head 250 within the uterine cavity 112 by pushing the finger grip member 286 of the actuator rod 252 axially toward the catheter head 250. The actuator rod 252 pushes the second collar 336 in a distal direction along the length of the end section 244 of the catheter 216. The movement of the second collar 336 pushes the leg 254b distally, causing the connecting member 274 to pivot about the tip 246 of the catheter 216 and to push the leg 254a in a proximal direction so that the first collar 330 moves in a proximal direction toward second collar 336. These movements also cause the distal ends 256a, 256b of legs 254a, 254b, respectively, to move outwardly away from the end section 244 of the catheter 216. Once the catheter head 250 is in its fully-opened configuration $Q_2$ (see FIG. 11), the connecting member 274 and the legs 254a, 254b are placed adjacent to, or, preferably, in contact with, the uterine cavity walls 122, 124 and 126 (see FIG. 12). The cryoablation procedure is then performed as described above.

The deployable cryosurgical catheters disclosed herein provide a means to treat multiple intrauterine sites, preferably, the entire endometrial tissue, in a single freezing step. Moreover, the disclosed cryosurgical catheters may conveniently be used with cryogenic probes that are presently known in the art and commercially available. The placement of the catheter head and the progress of the cryoablation procedure may be observed by non-invasive techniques, such as ultrasound imaging or MRI. The cryosurgical catheters have simple structures and may be made from materials that are widely available, making it possible to produce these devices at a relatively low cost.

It should be understood that the embodiments described herein are merely exemplary and that a person skilled in the art may make many variations and modifications without departing from the spirit and scope of the present invention. All such variations and modifications are intended to be included within the scope of the invention as defined in the appended claims. One practical variation involves the provision of a sterile sheath around the catheter and fully-closed catheter head such that the sheathed catheter may be transcervically inserted into the uterine cavity and the catheter head deployed therefrom. The actuater arm may be concealed within the sheath or it may be recessed into the outer walls of the probe. In another variation, a thermally-conductive fluid, such as a grease, may be placed within the channel inside of the end section of the catheter to improve the thermal contact between the end section of the catheter and the cold finger of the probe. In other variations, the finger grip may be extended proximally and provided with calibrated marks so that the catheter head may be deployed by known increments. Similarly, the catheter itself may be provided with calibrated marks to measure the depth to which the catheter is inserted. A mechanical deployment device may be attached to the proximal ends of the catheter or actuator arm to advance these elements by predetermined increments while improving the operator's ability to manipulate the cryosurgical device.

I claim:

1. An expandable apparatus for use with a surgical probe having a temperature-controlled portion, comprising:
   at least one thermally-conductive elongated extension member including a first extension member and a second extension member, said first extension member having a distal end and said second extension member having a distal end;
   thermal connection means for providing a thermal connection between said at least one extension member and the temperature-controlled portion of the surgical probe;
   attaching means for attaching said at least one extension member to the surgical probe such that said at least one extension member is movable between a closed configuration in which said at least one extension member is substantially parallel to the surgical probe and an open configuration in which said at least one extension member extends radially outward from the surgical probe, said attaching means comprising a tubular catheter having a distal end and a thermally-conductive section;
   moving means for moving said at least one extension member between said closed configuration and said open configuration; and
   a connecting member at said distal end of said catheter, said connecting member having a first end pivotably connected to said distal end of said first extension member and a second end pivotably connected to said distal end of said second extension member.

2. The apparatus of claim 1 wherein said thermal connection means comprises said thermally-conductive section of said catheter, said catheter being adapted to receive the temperature-controlled portion of the surgical probe therein such that the temperature-controlled portion of the surgical probe is thermally connected to said thermally-conductive section of said catheter.

3. An expandable apparatus for use with a surgical probe having a temperature-controlled portion, comprising:
   at least one thermally-conductive elongated extension member including a first extension member and a second extension member, said first extension member having a proximal end and a distal end and said second extension member having a proximal end and a distal end;
   thermal connection means for providing a thermal connection between said at least one extension member and the temperature-controlled portion of the surgical probe;
   attaching means for attaching said at least one extension member to the surgical probe such that said at least one extension member is movable between a closed configuration in which said at least one extension member is substantially parallel to the surgical probe and an open configuration in which said at least one extension member extends radially outward from the surgical probe, said attaching means comprising a tubular catheter having a distal end and a thermally-conductive section and said thermal connection means comprising said thermally-conductive section of said catheter, said catheter being adapted to receive the temperature-controlled portion of the surgical probe therein such that the temperature-controlled portion of the surgical probe is thermally connected to said thermally-conductive section of said catheter;
   moving means for moving said at least one extension member between said closed configuration and said open configuration; and
   a connecting member at said distal end of said catheter, said connecting member having a first end pivotably connected to said distal end of said first extension member and a second end pivotably connected to said distal end of said second extension member.

4. The apparatus of claim 3 wherein said connecting member is pivotably connected to said distal end of said catheter at a position between said first end of said connecting member and said second end of said connecting member.

5. The apparatus of claim 4 wherein said connecting member has a first segment including said first end and a second segment including said second end, said first segment being pivotably connected to said distal end of said catheter and movable independently from said second segment.

6. The apparatus of claim 4 wherein said moving means comprises a first collar having an axial opening, said first collar receiving said catheter within said axial opening such that said first collar is slidable along said catheter, the proximal end of said first extension member being pivotably connected to said first collar.

7. The apparatus of claim 6 wherein said moving means comprises a rod attached to said first collar, said rod being movable in a direction substantially parallel to said catheter.

8. The apparatus of claim 5 comprising a second collar having an axial opening, said second collar receiving said catheter within said axial opening of said second collar such that said second collar is slidable along said catheter, the proximal end of said second extension member being pivotably connected to said second collar.

9. The apparatus of claim 3 wherein said connecting member has a first end segment including said first end, a second end segment including said second end, and a middle segment positioned between said first end segment and said second end segment, said first end segment being pivotably connected to said middle segment, said second end segment being pivotably connected to said middle segment, and said middle segment being affixed to said distal end of said catheter.

10. The apparatus of claim 9 wherein said moving means comprises a collar having an axial opening, said collar receiving said catheter within said axial opening such that said collar is slidable along said catheter, the proximal end of said first extension member being pivotably connected to said collar and the proximal end of said second extension member being pivotably connected to said collar.

11. The apparatus of claim 10 wherein said moving means comprises a rod attached to said collar, said rod being movable in a direction substantially parallel to said catheter.

12. The apparatus of claim 3 wherein said moving means is adapted to selectively move said at least one extension member through a range of configurations intermediate between said closed configuration and said open configuration.

13. The apparatus of claim 3 wherein said first extension member, said second extension member and said connecting member are shaped to fit closely against said catheter in said closed configuration.

14. The apparatus of claim 3 wherein said apparatus includes a connecting element for securing said apparatus to the surgical probe.

15. The apparatus of claim 14 wherein said catheter has an open proximal end and said connecting element includes a compression mechanism for securing said proximal end of said catheter against the surgical probe such as to create a seal between said catheter and the surgical probe.

* * * * *